(12) United States Patent
Gizurarson

(10) Patent No.: US 6,647,980 B1
(45) Date of Patent: Nov. 18, 2003

(54) METHOD FOR ADMINISTRATION OF ACTIVE SUBSTANCES TO THE OLFACTORY REGION

(76) Inventor: Sveinbjörn Gizurarson, Kaplaskjólsvegur 37, IS-107 Reykjavik (IS)

( * ) Notice: Subject to any disclaimer, the term of this patent is extended or adjusted under 35 U.S.C. 154(b) by 0 days.

(21) Appl. No.: 09/446,931
(22) PCT Filed: Jul. 1, 1998
(86) PCT No.: PCT/DK98/00297
§ 371 (c)(1),
(2), (4) Date: Feb. 11, 2000
(87) PCT Pub. No.: WO99/01229
PCT Pub. Date: Jan. 14, 1999

(30) Foreign Application Priority Data

Jul. 1, 1997 (IS) .................................... 4516

(51) Int. Cl.[7] .............................................. A61M 11/00
(52) U.S. Cl. .................. 128/200.14; 604/514; 604/518
(58) Field of Search .............................. 604/19, 23, 24, 604/26, 36, 48, 500, 512, 514, 516, 518–520, 521, 57, 58, 82, 94.01; 128/200.14–200.24, 203.12, 203.19, 203.23, 207.18

(56) References Cited

U.S. PATENT DOCUMENTS

| | | | | |
|---|---|---|---|---|
| 3,762,409 A | * | 10/1973 | Lester | 128/200.14 |
| 4,054,622 A | * | 10/1977 | Lester | 128/200.14 |
| 5,116,315 A | | 5/1992 | Capozzi et al. | |
| 5,284,132 A | * | 2/1994 | Geier | 128/200.22 |
| 5,630,793 A | * | 5/1997 | Rowe | 604/20 |
| 5,683,361 A | * | 11/1997 | Elk et al. | 604/58 |
| 5,921,233 A | * | 7/1999 | Gold et al. | 128/200.22 |

FOREIGN PATENT DOCUMENTS

| | | |
|---|---|---|
| EP | 0 452 728 | 10/1991 |
| EP | 0 734 969 | 10/1996 |
| FR | 2130130 | 11/1972 |
| WO | WO93/02729 | 2/1993 |

* cited by examiner

Primary Examiner—Glenn K. Dawson
(74) Attorney, Agent, or Firm—Wenderoth, Lind & Ponack, LLP (57) ABSTRACT

The present invention relates to a method for administering a pharmaceutical preparation comprising at least one active substance to the olfactory region of a human. The method comprises administering a unit dose of the preparation by ejection from a nasal spray device (1) through a nostril of a human, the device and the pharmaceutical preparation being adapted so that the spray angle (3) is at the most 35°. The method is useful for the treatment of diseases affecting the olfactory organ, the brain and the central nervous system. The present invention also relates to a nasal spray device (1) comprising a pharmaceutical preparation. The pharmaceutical preparation preferably contains a viscosity enhancing agent and the pharmaceutical preparation preferably has a dynamic viscosity in the range of 5–300 cP.

50 Claims, 4 Drawing Sheets

METHOD FOR ADMINISTRATION OF ACTIVE SUBSTANCES TO THE OLFACTORY REGION

FIELD OF THE INVENTION

The present invention relates to a novel method for administration of active substances to the olfactory region of the nose. The method is useful for the treatment of diseases affecting the olfactory organ, the brain and the central nervous system.

BACKGROUND OF THE INVENTION

The transport of most bioactive materials from the systemic circulation to the brain are severely impeded by the mechanical and metabolic barrier known as the blood-brain-barrier. Only lipid-soluble molecules are able to enter the central nervous system in sufficient amounts, unless there are certain transport systems available. Due to this problem many drugs which do not cross this barrier, need to be injected directly into the subarachnoid space by lumbar puncture or cysternal puncture (Allison & Stach. *Drug Intell. Clin. Pharm.* 12;347:1978). Techniques for direct injection into the brain (intrathecal or subarachnoid injection) is associated with high risk for the patient, causing pain and hospitalisation, particularly in the case of repeated treatment. The method is poorly tolerated, requires the use of sterile syringes, may cause he risk of infection, induration, haemorrhage and/or slight necrosis at the injection site. The treatment is expensive and time consuming and may only be carried out by highly skilled personnel and in facilities that fulfil all requirements for brain surgeries.

The olfactory region has been the port for some serious infections as well as organic solvents, causing meningitis and brain damage, respectively. It has been shown that viruses, such as neurovirulent viruses, have been transported into the brain through the olfactory fibres and into the central nervous system. Other infections have been caused by Human erpetic encephalitis or the bacteria *Hemophilus influenzae*. Even parasites such as *Naegleria fowleri* are able to be transported across this area into the brain, causing death within 72 hours after infection (Lund et al. *J. Neuropath. Exp. Neurol.* 47;497:1988; Kristensson & Olsson. *Acta Neuropath.* 19;145:1971). The first evidence for a pathway between the olfactory mucosa and the central nervous system came from experiments with dyes, injected into the subarachnoid space of the brain passing into the nasal mucous membrane in low concentration (Yoffey. *J. Laryng.* 43;166:1949). Other substances were studied, which supported this theory, such as $^{32}P$ labelled phosphoric acid (Orosz et al. *Acta. Physiol. Acad. Sci. Hung.* 11;75:1957), colloidal gold ($^{198}Au$) (Czerniawska. *Acta Otolaryng.* 70;58:1970) and wheat germ agglutinin conjugated to horseradish peroxidase (Kristensen. *Acta Neuropath.* 19;145:1971). More recently it has been demonstrated that a direct transport of a bioactive material, such as insulin, occurs from the olfactory region of the nose to the brain (Gizurarson et al. *Int. J. Pharm.* 146;135:1997; and Gizurarson et al. *Drug Delivery.* in press).

WO 91/07947 describes the possibility for transporting neurologic and/or diagnostic neurologic agents to the brain by means of the olfactory neural pathway. WO 91/07947 also describes pharmaceutical compositions useful in the treatment and diagnosis of brain disorders.

WO 97/16181 relates to a method for enhancing the delivery of L-dopa to the brain of a mammal by administering water-soluble prodrugs of L-dopa intranasally.

U.S. Pat. No. 5,525,329 provides a method for enhancing the sense of smell involving application of an inhibitor of phosphodiesterase to the olfactory epithlium.

However, using the conventional techniques (such as described in e.g. WO 91/07947) for administration of drugs into the nasal cavity it has been found by the present inventor that it is nearly impossible to get access to the olfactory region. Nearly means, as will be apparent from the examples provided herein, that conventional spray techniques result in less than 0,4% of the formulation having access to the olfactory region. Furthermore, nasal drops and nasal catheter did not provide access to this region.

Clearly, there is a need for improved methods, including suitable nasal devices and suitable pharmaceutical preparations, for administering effective amounts of active substances to the olfactory region, thereby improving the possibility of administering active substances to the brain and to the central nervous system.

Thus, the main object of the present invention is to provide a method for administering active substances to the olfactory region of a human in clinically relevant amounts.

SUMMARY OF THE INVENTION

These and other goals are met by the present invention which in a first aspect is directed to a method for administering a pharmaceutical preparation comprising at least one active substance to the olfactory region of a human, the method comprising administering a unit dose of the pharmaceutical preparation by ejection from a nozzle of a spray device through a nostril of the human, the device being positioned so that the exit orifice of the nozzle is positioned approximately at the orifice of the nostril or in the *vestibulum nasi*, the device and the pharmaceutical preparation being adapted so that the spray angle is at the most 35°.

Another aspect of the invention relates to a nasal spray device containing an amount of a pharmaceutical preparation and being adapted for ejecting a unit dose of the pharmaceutical preparation from a nozzle of the spray device through a nostril of a human on actuation of the device, the device and the pharmaceutical preparation being adapted so that the spray angle is at the most 35°.

A further aspect of the invention relates to a nasal spray device containing an amount of a pharmaceutical preparation and being adapted for ejecting a unit dose of the pharmaceutical preparation from a nozzle of the spray device through a nostril of a human on actuation of the device, the pharmaceutical preparation being a liquid having a dynamic viscosity at 25° C. in the range of 5–300 cP.

Further aspects appear from the claims and the following description.

DETAILED DESCRIPTION OF THE INVENTION

The nose contains two nasal cavities separated from one another by the nasal septum. Each cavity opens in the front by a nostril (or naris). Bone and, to a lesser extent, cartilage and, to a small degree, dense connective tissue provide rigidity to the walls, the floor and the roof of the nasal cavities and thereby prevent their collapse on inspiration. Three plates of bone, arranged one above the other like shelves, are disposed along the lateral wall of each nasal cavity. They are, however, not flat but curve downward. Due to their characteristic form, these plates of bone are called the superior, the middle and the inferior conchae.

Each nasal cavity is divided into two parts: 1) a vestibule, the widened part of the passageway encountered just behind the nostrils, and 2) the remainder of the cavity, called the respiratory portion. The mucous membrane of the respiratory portion lining the upper parts of the sides and the roof of the posterior part of each cavity constitutes the so-called olfactory region. As mentioned above, there are two olfactory regions, one in each of the two nasal cavities and the mucous membrane lining the nasal cavities in the two olfactory regions constitutes the so-called olfactory organ. The nerve cell bodies present in the epithelium of the mucous membrane at this site are highly sensitive in their ability to be selectively stimulated by odours of different kinds.

The mucous membrane of the olfactory region is of a yellow hue. It is disposed so as to line most of the uppermost part of the roof of each nasal cavity, beginning in front of the anterior termination of the superior concha and extending backward for about 1 cm. From the roof it extends down both sides of each nasal cavity: On the lateral side it extends so that it covers most of the superior concha, and on the medial side it extends for about 1 cm down the nasal septum. A detailed description of the anatomy of the nose as well as descriptions regarding the microscopic structure and the relation between function and structure of the olfactory organ can be found in standard textbooks in histology and anatomy, such as in "Histology", 7. Ed. A. W. Ham, J. B. Lippinocott Company, Philadelphia, U.S.A., 1974.

Figure 1:
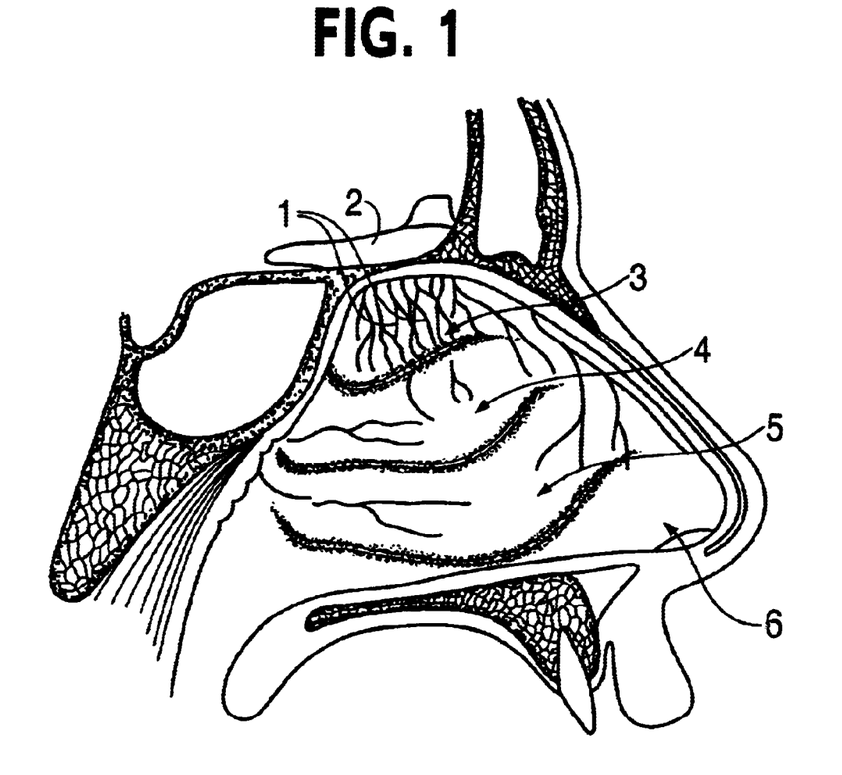
FIG. 1: Drawing of the human nose cavity showing the location of various parts in the nasal cavity.

FIG. 1 shows a drawing of the nasal cavity of a human. 1 is the olfactory nerves present in the olfactory region and 2 is the olfactory bulb. 3, 4 and 5 shows the superior, the middle and the inferior conchae, respectively, and 6 shows the nasal vestibule (*vestibulum nasi*).

As mentioned above, the present invention relates to a method for administering an active substance, such as drugs, peptides, proteins, diagnostics, antibodies and/or gene manipulated micro-organisms, to the olfactory region of a human and, consequently, the present invention provides a direct pathway to the olfactory mucosa and from there into the olfactory bulb and from there to the interconnected areas of the brain such as hippocampal formation, amygdaloid nuclei, nucleus basalis of Myenert, locus ceruleus, and the brainstem raphe nuclei. The method of the invention also provides a pathway to the cerebrospinal fluid, corpus plexus and the arachnoid area of the brain.

Therefore, it will be acknowledged by the person skilled in the art that the method according to the invention may be used in the treatment or prophylaxis of conditions or disorders in the brain or in the central nervous system.

Figure 2:
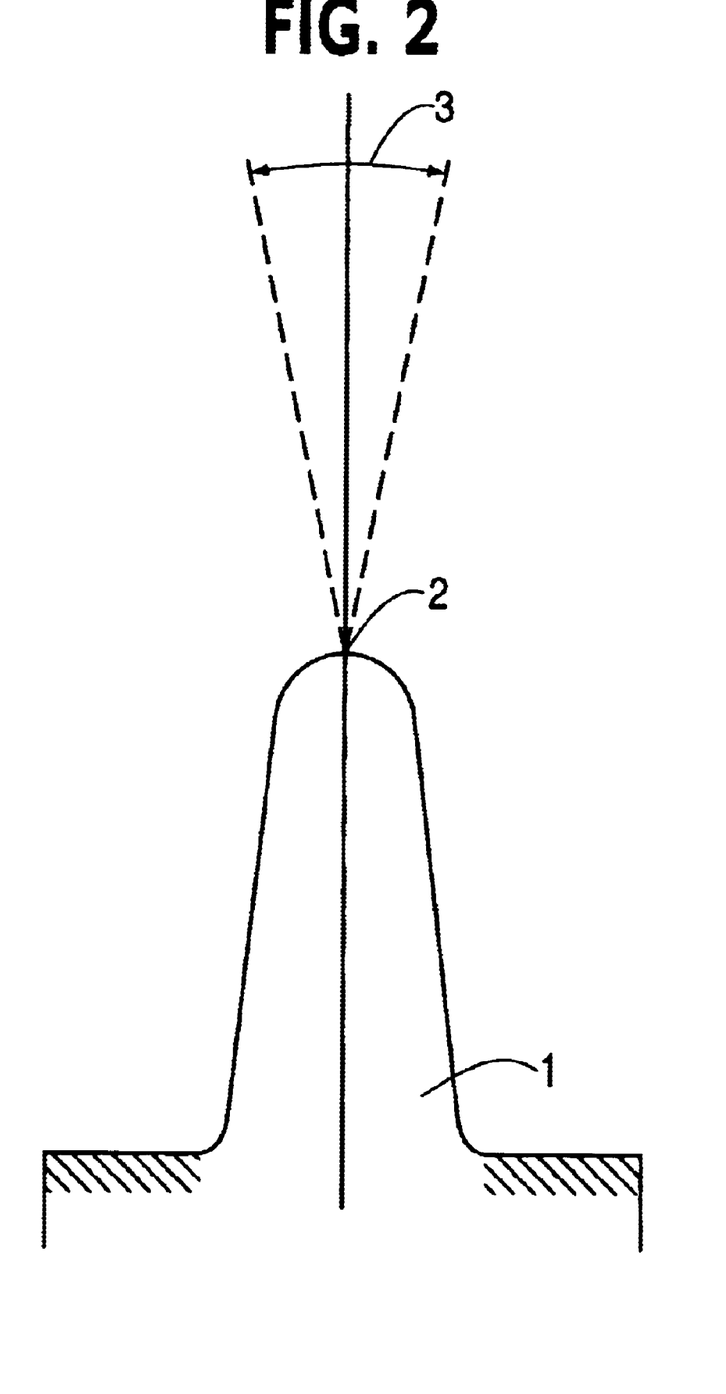
FIG. 2: Definition of the term "spray angle" as used herein.

Surprisingly, it has been found by the present inventor that in order to get access to the olfactory area, the active substance (which is usually present in a pharmaceutical preparation) should be administered in such a way through the nostril that the "spray angle" as defined in FIG. 2. is as small as possible. As mentioned above, the spray angle is at most 35°. Preferably the spray angle should be adapted so that at least 50% (w/w) of the pharmaceutical preparation comprising the active substance is delivered to a nostril with a spray angle of at the most 15°. It is more preferred that at least 60%, still more preferred at least 70% (w/w), such as at least 75% (w/w), e.g. at least 80% (w/w), more preferably at least 85% (w/w), such as at least 90% (w/w), e.g. at least 95% (w/w), and in particular at least 99% (w/w), such as substantially all of the pharmaceutical preparation, is delivered to a nostril with a spray angle of at the most 15°, more preferably at the most 14°, e.g. at the most 13°, still more preferably at the most 12°, such as at the most 11°, e.g. at the most 10°.

The above-mentioned requirements to the spray angle are independent of whether the active substance (or a pharmaceutical preparation comprising the active substance) is administered as droplets in the form of spray (as powder or solution), or as a "splash" where the formulation may be a gel, an ointment or a viscous solution.

In the present context the term "splash" is intended to mean an ejected stream which is more coherent in the dynamic appearance than a spray, normally due to a higher viscosity resulting in larger drops or larger coherent domains in the dose ejected.

The term "spray angle" is defined with reference to FIG. 2: 1 is the administration device (*vide infra*), 2 is the outlet orifice of the device, and 3 indicates the above mentioned "spray angle".

As will be understood by the skilled person, it is of importance that the active substance is delivered in, or "close" to the nostril. The present inventor has found that conventional nasal devices (such as Pfeiffer "Unit Dose" Open System, No. 01-14398, Pfeiffer GmbH, Germany) may be used in the method according to the invention, provided that the dynamic viscosity of the pharmaceutical preparation to be administered is increased and/or the diameter of the outlet orifice of the device is increased. For administration purposes the device may be positioned so that the exit orifice of the nozzle of the device is positioned approximately at the orifice of the nostril or in the *vestibulum nasi* at the most about 2.0 cm, preferably at the most about 1.50 cm, such as at the most about 1,25 cm, in particular at the most about 1 cm from the orifice of the nostril, or just at the nostril (or a few mm below, which is, however, not particularly preferred). Thus, it is evident that unnecessary inconvenience and unpleasantness for the patient can be avoided as the present invention provides a method for administering an active substance to the olfactory region of the nose without introducing nasal devices, syringes, needles and the like deeply into the nasal cavity.

In order to assess the suitability of the pharmaceutical preparation and/or the device in the method for the invention, the present inventor has provided an in vitro test which can easily be carried out by the person skilled in the art. The above-mentioned in vitro test is described in detail in "Experimental" in the section entitled "In Vitro Delivery Test".

The user of the device simply actuates the device when the device is held in such a position that the nozzle thereof "aims" in the direction of the olfactory region, which is the case when it "aims" or points in the direction of the middle of the top of the skull.

In preferred embodiments of the invention, the device and the pharmaceutical preparation should be adapted so that in the "In Vitro Delivery Test" described herein, at least 50% of the unit dose will be deposited in a region having a diameter of at the most 1,8 cm on an absorbent surface perpendicular to the direction of at a distance of 3.0 cm from the locus from which the unit dose is delivered, preferably, at least 50%, more preferably at least 60% and even more preferably at least 75% of the unit dose will be deposited in a region having a diameter of at the most 1.5 cm (more preferably at the most 1.2 cm, still more preferably at the most 1.0 cm and still more preferably at the most 0.9 cm). It is, of course, preferred that substantially the full amount (i.e. above 80%, preferably above 85%, e.g. above 90%, in particular above 95%) of the dose of the pharmaceutical preparation ejected from the nozzle of the device will be deposited in a region having a diameter of at the most 1.8 cm, such as at the most 1.6 cm, e.g. at the most 1.4 cm, preferably at the most 1.2 cm, in particular at the most 1.0 cm.

The active substance to be administered according to the method of the invention may be any active substance which is capable of treating, detecting, or preventing diseases or disorders in the olfactory region, in the brain, or in the central nervous system.

Accordingly, in the present context the term "active substance" is intended to cover such substances which are capable of treating, detecting, or preventing diseases or disorders in the olfactory region, in the brain, or in the central nervous system.

The amount of the active substance to be delivered should be an effective amount with respect to the desired effect of the treatment or the desired reliability of the response to a diagnostic test or detection. This does not necessarily mean that all or a predominant proportion of a unit dose ejected must be deposited on the mucosa of the olfactory region (although that would, of course, in principle, be preferred). What is essential is that by use of the principle of the present invention, it becomes possible, realistic and pharmaceutically acceptable to deliver an effective amount of an active substance to the olfactory region.

Examples of specific diseases or disorders to be treated according to the method of the invention are e.g. Alzheimer's disease, Parkinson's disease, brain tumours, brain cancer, AIDS, schizophrenia, affective disorders such as depression and mania, anxiety disorders, dependency on addiction diseases, nerve damage from cerebrovascular disorders such as stroke, and brain changes associated with ageing, obesity, epilepsy, amnesia, sleep disorders, brain infections such as bacterial, viral, prion or parasitic infections or meningitis and other diseases affecting the brain. The method of the invention may also be used to treat diseases affecting the olfactory area such as loss of smelt.

Accordingly, active substances which are of particular interest, i.e. active substances which may be used for medical and/or prophylactic treatment of the above-mentioned diseases affecting the olfactory region or the brain, are, e.g., antiviral substances; antiprion substances; antibacterial substances, antineoplastic substances, antiparasitic substances, anti-inflammatory substances such as ibuprofen, indometchacin, naproxen, diclofenac, tolfenamic acid, piroxicam, and the like; antidepressant substances such as imipramine, nortriptyline, pritiptylene, and the like; antifungal substances such as miconazol, ketoconazole, amphotericin B, nystatin, mepyramin, econazol, fluconazol, mycostatin, and the like. The active substance to be administered may also act as a neurotransmitter, neuromodulators, nootropic, hormone, hormone releasing factor, hormone receptor agonist or antagonist. The active substance may also be an activator or inhibitor of a specific enzyme, an antioxidant, a free radical scavenger, a metal chelating agent, or an agent which alters the activity of ion channels of brain cell membranes, for example nimodipine. The active substance may further be any substance which is capable of acting as a stimulant, sedative, hypnotic, analgesic, anticonvulsant, antiemetic, anxiolytic, tranquilliser, cognition enhancer, agents preventing or healing amnesia, metabolic stimulator or inhibitor, appetite stimulator or inhibitor and/or narcotic antagonist or agonist. Moreover, the active substance may be any substance found to be deficient in conjunction with the brain disorder being treated or prevented, for example, nutrients such as glucose, ketone bodies, and the like, or metabolic precursors such as lecithin, choline or acetyl coenzyme A for producing neurotransmitters for the treatment of Alzheimser's disease or insulin for the treatment of obesity. The active substance may also be an antibody suitable for the treatment of viral, bacterial, prion, parasitic infections or tumours and/or cancer or for diagnosis of brain diseases or disorders where polyclonal or monoclonal antibodies and/or/with biochemical markers characteristic of the diseases or disorder are used. Such diagnostic antibodies may be labelled with any suitable labelling agent. Gene manipulated micro-organisms may also be used for the treatment of tumours and/or cancer in the olfactory region or the brain.

Furthermore, in some situations the concha may be enlarged, especially in allergic rhinitis. In order to pretreat or treat this enlarged concha, especially concha nasalis media, the enlarged concha may be treated with an active substance having adrenergic, antihistamin or corticosteroid effect such as ephedrin, metaoxedrin, naphazolin, tetrahydrozolin, oxymetazolin, xylometazolin, budesonid, flunisolid, beclometasonidipropionat, cocain etc, in accordance with the method disclosed herein.

The active substance may be applied alone (in which case it alone constitutes the pharmaceutical preparation) or in combination with other substances. Thus, if the active substance has the appropriate physico-chemical properties (vide infra) the active substance may be administered alone. This may be the case where the active substances is a liquid or is in the form of a powdered substance. In most cases, however, the active substance is preferably present in a pharmaceutical preparation together with other constituents.

Pharmaceutical preparations which are suitable for use in the method according to the invention may be in the form of fluid, semisolid, or solid preparations such as powder, including microencapsulated powder, granulates, microspheres and nanospheres; liquids including solutions, dispensions, emulsions and suspensions; liposomes, gel, hydrogels, foam, ointment or gas. Preferably, however, the preparation is a liquid preparation, preferably an aqueous solution.

For single unit dose administration to the olfactory cavity, the volume administered should not exceed 300 $\mu$l per nostril, preferably the volume should not exceed 200 $\mu$l per nostril, in particular the volume should not exceed 100 $\mu$l per nostril.

The method according to the invention may, however, also be used to provide a continuous drug delivery over a certain period of time, e.g. as a pulsate matter to the olfactory region. Such delivery technique may be regarded as intraolfactory infusion which may be used for the delivery of drug over a period of several minutes to several days.

It will be understood that the nasal spray device will be any device which is suitable for ejecting a dose of the preparation in the manner defined herein. A large number of nasal spray devices are known, and the person skilled in the art will be able to combine and modify or adapt the pharmaceutical preparation and/or the particular device so that the critical criteria with respect to the spray angle are fulfilled, using the instructions herein and testing/calibrating the combination of the device and the preparation by the in vitro test defined herein. A number of suitable modifications of the devices may be made, such as supplying the device with guide faces for contacting the nose or the upper lip part to facilitate directing the nozzle against the olfactory region. As a general rule, however, it will be sufficient to associate the device with suitable instructions for use, assisting the user in operating the device properly to obtain the high amount of the preparation delivered at the olfactory region, possibly aided by an olfactory substance as mentioned below.

Nasal spray devices can be disposable devices containing a unit dose. Examples of such devices are the devices used in the examples herein and illustrated in the drawings. Alternatively, they can be devices which are used several times and which either contain an amount of the pharmaceutical preparation corresponding to a multitude of unit dosages or are supplied from a container containing such an amount; such devices used several times can be provided with means for metering out the unit dose in connection with the administration.

Figure 3:
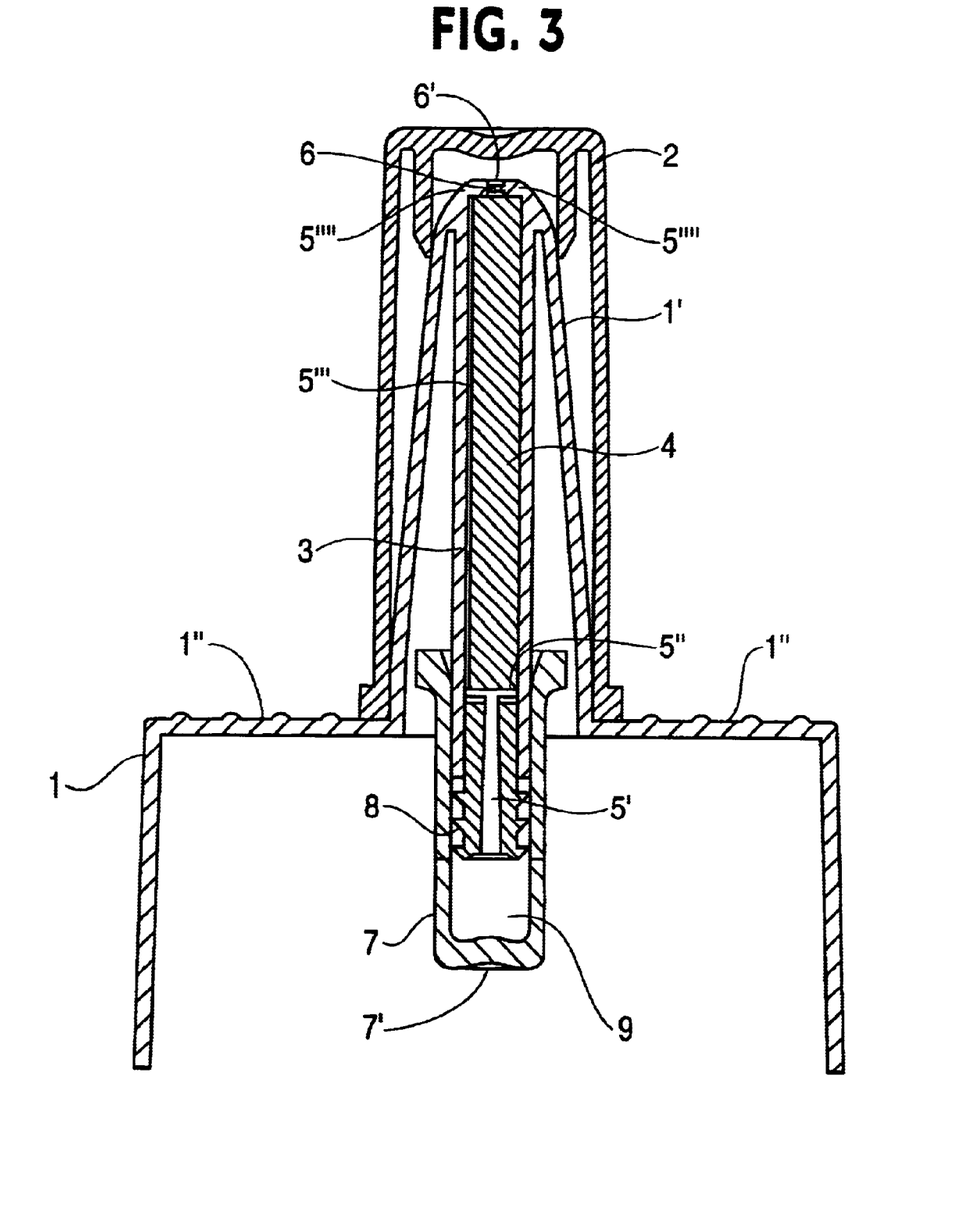
FIG. 3: Sectional view of a commercial nasal spray device used in the experiments described herein.

FIG. 3 shows a sectional view of a commercial nasal spray device which may be used in the method of the invention and which has been used in the examples herein. A body 1 of polypropylene has a rounded tip 1' adapted to be held close to a nostril orifice or inserted into the nostril (i.e. into the vestibulum nasil) of a human. When the device is not in use, the tip is covered by a polyethylene cap 2. A central inner tube 3 extending from the interior top part of the tip part receives a cylindrical polyethylene rod 4 defining therein a central channel 5' which communicates with a transverse channel 5" which on its part communicates with a longitudinal channel 5'" defined by an inner wall part of the tube 3 and the wall of a longitudinal groove in the rod 4. The channel 5'" communicates with an annular channel 5"" defined by a groove in the interior upper part of the tip part 1' and the top end surface of the rod 4. A central nozzle 6 defined in the upper end of the part 1' has an orifice part 6' having a diameter of 0.25 mm. A cylindrical glass container 7 of the outer diameter 6.6 mm is slidingly and removably fitted around the lower part of the tube 3 and a lower part of the rod 4 provided with sealing fins 8.

In the use of the device, a portion of the preparation to be sprayed from the device is placed in the interior 9 of the container 7, and the container is fitted on the tube 3 as shown. The device is normally held by means of one finger at each of the horizontal areas 1" and the thumb at a bottom part 7' of the glass container. By pressing the glass container upwardly, the dose in the container is sprayed out through the nozzle orifice 6'. The device is a disposable device for spraying a single unit dose contained in the device. The dead volume of the device is a bout 10 μl, so that when the desired unit dose is, e.g., 50 μl, the amount filled in the device is 60 μl.

As mentioned above, the pharmaceutical preparation is preferably a liquid preparation, and it should be understood that in cases where a conventional nasal spray device is employed in the method of the invention, the physicochemical properties of the liquid preparation are of utmost importance. As will be evident from the examples provided herein, the key parameter is the dynamic viscosity of the liquid pharmaceutical preparation. It has been found by the present inventor that in order to deliver clinical relevant amounts of an active substance to the olfactory region of a human, the dynamic viscosity of the liquid preparation should be increased compared to the dynamic viscosity of water.

It is presently believed that an increased dynamic viscosity of the preparation implies that larger drops are formed which in turn leads to less atomisation of the drops. Consequently, the preparation can be delivered from the nasal device in a more "coherent" way (so-called "splash") so that the spray angle is significantly reduced compared to preparations having a dynamic viscosity close to the dynamic viscosity of water. In other words: In cases where a conventional nasal device is used in the method of the invention (i.e. when the diameter of the nozzle orifice is about 0.25 mm) the viscosity of the liquid pharmaceutical preparation should preferably be adjusted so as to obtain a dynamic viscosity (vide infra) in order to fulfil the requirements set forth above with respect to the in vitro test and the spray angle.

Thus, in a very interesting embodiment of the invention the liquid pharmaceutical preparation comprises at least one viscosity enhancing agent. Examples of suitable viscosity enhancing agents are for example polysaccharides, including cellulose derivatives such as hydroxypropyl cellulose, hydroxypropyl methylcellulose, hydroxyethyl methylcellulose and carboxymethylcellulose and salts thereof, such as sodium carboxymethylcellulose. Other examples of suitable viscosity enhancing agents are acrylic polymers such as polyacrylic acids and polymethacrylates, e.g. carbopol, poly(hydroxyethyl methacrylate), poly(methoxyethyl methacrylate) and poly(methoxyethoxyethyl methacrylate); proteins such as gelatine; high average molecular weight polyhydroxy compounds such as polyvinyl alcohols; higher alcohols such as cetyl alcohol and stearyl alcohol; glycols such as propylene glycol and ethylene glycols (PEGs) including PEG 200, PEG 300, PEG 400, PEG 500, PEG 600, PEG 700, PEG 800, PEG 900, PEG 1000, PEG 1450, PEG 3350, PEG 4500 and PEG 8000 and derivatives thereof; sorbitol, glycerine, and polysorbates such as Tween 20 to 85.

The viscosity enhancing agent should be present in the liquid preparation in such a concentration that, on the one hand, the preparation has a sufficient dynamic viscosity (vide infra), and on the other hand, the viscosity of the preparation is not becoming so "thick" that the preparation sticks to the nasal device and ejection of the preparation from the device is impeded. Accordingly, it is difficult to give general guidelines concerning the actual concentration of viscosity enhancing agent in the liquid pharmaceutical preparation as this concentration depends on the viscosity enhancing agent used in the preparation as well as the concentration of other excipients which may be present in the liquid preparation.

The concentration of viscosity enhancing agent will, however, normally be within the range of from 0.01% (w/v) to 10% (w/v), preferably in the range of 0.05% (w/v) to 5% (w/v). In any case, the amount of viscosity enhancing agent in the liquid preparation should be sufficient to secure that the dynamic viscosity of the liquid pharmaceutical preparation (measured at 25° C.) is higher than the dynamic viscosity of water (the dynamic viscosity of water is about 1 cP at 25° C.), e.g. at least 5 cP, preferably in the range of 5–300 cP, such as in the range of 5–100 cP. In particular preferred embodiments of the invention the dynamic viscosity of the liquid pharmaceutical preparation is in the range of 10–75 cP, preferably in the range of 10–50 cP, such as in the range of 20–50 cP.

It should be noted that the unit "cP" (centipoise) may be converted to "$kg \times m^{-1} \times s^{-1}$" by multiplication by $10^{-3}$.

In a particular interesting embodiment of the invention, the pharmaceutical preparation further comprises an odorant (i.e. an "olfactory indicator"). Such a substance may be incorporated in the pharmaceutical preparation or in a calibration preparation having the same physico-chemical properties (viscosity, surface tension, density, evaporating energy, etc.) as the pharmaceutical preparation. Preferably, however, the odorant is a substance of such properties, and incorporated in the pharmaceutical preparation in such an amount, that it will only be perceivable when an effective amount of the active substance has reached the olfactory region. The odorant is typically incorporated in the pharmaceutical preparation in an amount of at the most 0.01% (w/w), preferably lower, such as at the most 0.001% (w/w). Examples of suitable odorants for use in the method according to the invention are for example terpenoids such as cetralva and citronnellol, aldehydes such as amyl cinnamaldehyde and hexyl cinnamaldehyde, esters such as octyl isovalerate, jasmines such as C1S-jasmine and jasmal, musk 89, vanillin, and aetherolum menthae piperitae.

Pharmaceutical preparations suitable for use in the method of the present invention may be prepared in a manner well-known to the person skilled the art, e.g. as generally described in "Remington's Pharmaceutical Sciences", 17. Ed. Alfonso R. Gennaro (Ed.), Mark Publishing Company, Easton, Pa., U.S.A., 1985 and more recent editions, and in the monographs in the "Drugs and the Pharmaceutical Sciences" series, Marcel Dekker.

In addition to the viscous properties already discussed, the liquid pharmaceutical preparation should preferably possess the following physico-chemical characteristics: A surface tension in the range of from about 16 to about 90 mN/m; a density in the range of from about 0.7 to about 1.3 g/ml; and a pH in the range of from about 4.0 to 8.5.

The liquid pharmaceutical preparation may further comprise one or more excipient(s) such as surfactants, absorption promoters, water absorbing polymers, substances which inhibit enzymatic degradation, organic solvents, oils, pH-adjusting agents, solubilizers, stabilisers, HLB (Hydrophile-Lipophile Balance)-adjusting agents, preservatives, osmotic pressure-adjusting agents, propellants, etc. The above-mentioned excipients are all selected in accordance with conventional pharmaceutical practice in a manner understood by the persons skilled in the art of formulating pharmaceuticals.

Examples of surfactants which may be incorporated in the liquid preparation are e.g. non-ionic surfactants such as bile salts and derivatives thereof, fusidic acid and derivatives thereof, polysorbates such as Tween 20 to 80, e.g. Tween 20, Tween 40, Tween 60 and Tween 80, fatty alcohols such as lauryl alcohol, cetyl alcohol and stearyl alcohol, spans such as sorbitan monopalmitate, polyethylene glycol derivatives such as nonoxynol 9 and octoxynol 9; anionic surfactants such as sodium, potassium and ammonium salts of fatty acids having a chain length of from 12 to 18 carbon atoms, sulfonates such as sodium bis-(2-ethylhexyl)sulfosuccinate, sulphates such as sodium lauryl sulphate; and cationic surfactants such as quaternary ammonium salts.

Absorbing promoters may be selected from polyoxyethylene alcohol ethers, bile salts and derivatives thereof, fusidic acid and derivatives thereof, fatty acids such as oleic acid, lecitin, lysolechitins, polysorbates such as Tween 20–85, mono-, di- and triglycerides, chitosan, and cyclodextrins.

Specific examples of water absorbing polymers are e.g. polyethylene glycol 200–7500 and derivatives thereof, polyvinylpyrrolidone, polyacrylic acid, propylene glycol, proteins such as gelatine, cellulose and derivatives thereof.

Substances which are capable of inhibiting enzymatic degradation are e.g. aprotinin, DFP, and carbopol.

Examples of suitable oils are e.g. vegetable oil, soybean oil, peanut oil, coconut oil, maize oil, olive oil, sunflower oil and Miglyols.

In certain embodiments the preparation for use in the method of the invention may also comprise one or more pharmaceutically acceptable pH-adjusting agents in order to adjust the pH of the preparation to the desired pH. Any pharmaceutically acceptable pH-adjusting agent, which will be known to the person skilled in the art, may be used, e.g. lactic acid, citric acid, phosphoric acid, acetic acid, hydrochloric acid, nitric acid, sodium or potassium metaphosphate, sodium or potassium phosphate, sodium or potassium acetate, ammonia, sodium carbonate, sodium or potassium hydroxide, dibasic sodium phosphate, sodium borate, etc.

In should be understood that the liquid preparation is preferably (but necessarily) an aqueous preparation. Therefore, in order to dissolve more hydrophobic substances it may be necessary to add various amounts of solubilizers to the preparation. Thus, specific examples of suitable solubilizers are e.g. alcohols such ethyl alcohol, isopropyl alcohol; propylene glycol; glycofurol such as the commercially available glycofurol 75 (Chemical Abstract Registration No. 9004 76-6]); and polyethylene glycol (PEG) 200–8000, such as PEG 200, PEG 300, PEG 400, PEG 500, PEG 600, PEG 700, PEG 800, PEG 900, PEG 1000, PEG 1450, PEG 3350, PEG 4500 and PEG 8000.

Examples of HLB-adjusting agents are e.g. Tween 20–85, Span 20–80, Brij 30–98, and acacia.

Examples of specific preservatives which may be incorporated in the preparation are e.g. parabens such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodoprpynyl butylcarbamate, EDTA, benzylalcohol, phenol, and benzalkonium chloride.

Examples of suitable osmotic pressure controlling agents are for example dextrose, sucrose, alkali metal halogenides such as sodium chloride, and mannitol; and examples of a suitable stabilisers are e.g. cyclodextrines.

Suitable propellants may be selected from e.g. dichlorodifluoromethane, dichlorotetrafluoroethane, trichloromonofluoromethane and other non-ozone damaging propellants, and for air displacement nitrogen and/or other non-reactive and non-toxic gases may be used.

Although the presently preferred form of the preparation is a liquid, it may also be in the form of a powder such as microencapsulated powder, granulates, microspheres and nanospheres.

The powder may have a mean particle size in the range of from about 0.10 µm to about 100 µm, preferentially in the range of from about 0.5 µm and 25 µm, and may contain the active substance in combination with excipients such as substances which inhibit enzymatic degradation, propellants, fillers, air displacement, etc.

Examples of substances which inhibit enzymatic degradation are e.g. aprotinin, DFP, and carbopol.

Propellants may be selected from dichlorodifluoromethane, dichlorotetrafluoroethane, trichloromonofluoromethane and other non-ozone damaging propellants. Examples of suitable fillers are e.g. microcrystalline cellulose and lactose and for air displacement nitrogen or other non-reactive and non-toxic gases may be used.

In general, i.e. independent of the actual physical form of the pharmaceutical preparation, the preparation comprising the active substance may also contain components that may facilitate the transfer of the active substance to the brain.

As indicated above, the radius of the outlet orifice of the employed device may be increased compared to conventional devices, and this may be the only adaptation or may be combined with an adaptation, such as a viscosity increase, of the pharmaceutical preparation. Preferably, the diameter of outlet orifice of the employed device should be in the range from 0.1 to 1.0 mm, such as in the range from 0.2 to 0.8 mm, preferably in the range from 0.25 to 0.75 mm. As will be understood from the examples provided herein, it will usually be necessary to increase the diameter of the outlet orifice of the device if the dynamic viscosity of the pharmaceutical preparation is low. Thus, for pharmaceutical preparations having a dynamic viscosity close to the dynamic viscosity of water it will usually be necessary to increase the diameter of the outlet orifice to a value above 0.25 mm, preferably to a value above 0.3 mm, such as above 0.4 mm, preferably to a value above 0.5 mm, in particular to a value above 0.6 mm, e.g. to a value above 0.65 mm.

The following physical considerations may be of assistance in modifying the flow parameters of the device:

In general, i.e. irrespective of whether the viscosity of the liquid preparation is increased and/or the radius of the outlet of the device is increased, the Reynolds number of the liquid formulation should not be too high, when calculated according to Formula I:

$$Re=(\rho\tau d)/\eta \qquad \text{(I)}$$

wherein Re is the Reynold's number; ρ is the density of the liquid preparation; τ is the outlet velocity of the liquid preparation from the device; d is the outlet diameter of the device; and η is the dynamic viscosity of the liquid preparation.

It is evident from the Formula I above that an increase in the viscosity will reduce the Reynold's number defined above.

In a similar way, an increase in the diameter of the outlet hole would lead to a decrease in the velocity of the liquid preparation. In fact, the velocity of the liquid preparation at the outlet is dependent on the square of the diameter. Thus, an increase in the diameter would lead to an overall reduction in Reynold's number.

As will be acknowledged by the skilled person, the inlet velocity of the liquid preparation at the orifice of the nostril is of importance.

For small particles a velocity of the order of 5 times the gravitational force may be required. The general formula of the velocity v and position l at time t of a particle describing a linear motion in a direction opposite to the force of gravity, which gives a conservative estimate of the combined influence of gravity and drag force on the particle, is given by $$v(t) = v_0 - \int_0^t \left(g + \frac{F_D}{M}\right) dt$$

$$l(t) = \int_0^t v(t)\,dt = v_0^t - \frac{1}{2}gt^2 - \int_0^t \int_0^t \left(\frac{F_D}{M}\,dt\right) dt$$

where $v_o$ is the inlet velocity at time t=0, g is the gravitational acceleration, $F_D$ is the drag force on the particle and M is the mass of the particle. The general formulation of the drag force $F_D$ is $$F_D=\tfrac{1}{2}\rho_{air}v(t)^2A_fC_D$$

where $\rho_{air}$ is the density of the air, $A_f$ is the face area of the particle and $C_D$ is the drag coefficient.

The face area and the particle mass can be found if it is assumed that the particles are spherical:

$$A_f=\tfrac{\pi}{4}D^2$$

$$M=\rho_p\tfrac{\pi}{6}D^3$$

where $\rho_p$ is the density of the particle material and D is the diameter of the particle.

The ratio of the drag force to the mass can then be reduced to $$\frac{F_D}{M} = \frac{\rho_{air}}{\rho_P}\frac{3}{4}\frac{v(t)^2C_D}{D}$$

The drag coefficient of a sphere can be found from an empirical extension of Stokes law that is valid if Re<100 which is a reasonable upper limit, considering the preferred particle diameters and velocities:

$$C_D = \frac{24}{Re}\left(1 + \frac{3}{16}Re\right)^{1/2}$$

where the Reynolds number Re is defined as $$Re = \frac{\rho_{air}v(t)D}{\mu_{air}}$$

with $\mu_{air}$ being the coefficient of dynamic viscosity of air. The equations for velocity v and position l can be solved numerically to provide a minimum inlet velocity for particles of a given diameter that are to traverse a given distance and retain a given minimum residual velocity when the given distance is traversed. This residual velocity could be of the order of 0.1 to 0.5 m/s. The applicability range of these expressions can be extended to cover slightly non-spherical particles by replacing the diameter D with the hydraulic diameter $D_h$ of the particles but the validity of the expressions will decrease the more the shape of the particles deviates from a spherical shape.

Quite generally, however, the combination of the device and the preparation should be so adapted that the spray angle is within the limits defined, and as mentioned above, the in vitro test is an excellent tool in the development.

As will be understood, details and particulars concerning the novel device aspects of the invention, as well as the use of the pharmaceutical preparation, will be the same as or analogous to the details and particulars of the method discussed above in accordance with the method aspects of the invention, and this means that whenever appropriate the statements concerning the method discussed in detail herein apply mutatis mutandis to the novel devices according to the invention as well as to the use of the pharmaceutical preparation according to the invention.

EXPERIMENTAL

The "In Vitro Delivery Test"

The nasal spray device comprising the pharmaceutical preparation to be delivered is placed so that the exit orifice of the device points straight up. A water absorbent surface which is adapted to receive and substantially immediately absorb a spray or droplets, in the present case preferably a suitable ink jet paper (Kynlux 80 gr/m² paper, obtainable from UPM Kymmene Co., Finland) is placed 3 cm above, and perpendicular to, the exit orifice of the device.

A unit dosage of the pharmaceutical preparation is ejected from the device (and thereby applied to the water absorbent surface) by normal actuation of the device.

1) For the Determination of the Diameter of a Region Within Which Substantially all of the Unit Dose is Delivered:

The smallest circle which encompasses the area of the water absorbent surface which has been wetted by the pharmaceutical preparation is drawn and the diameter of the circle is measured. In most cases, there will be a few small wetted spots outside the wetted main area; these are not included in the area encompassed by the circle.

2) For the Assessment of the Delivery of at Least a Particular Percentage of the Unit Dose Within a Region of a Particular Diameter:

A circle of the specified diameter is drawn, the centre being the centre of the deposited unit dose. The circle is excised from the surface. The active substance is extracted from the excised area and is measured quantitatively by spectrophotometry.

EXAMPLE 1

Accessibility to the Olfactory Region—the Influence of Viscosity

An aqueous solution containing 1.0% (w/v) caffein (obtained from Apodan, Denmark) was (1) administered using a conventional nasal spray device (Pfeiffer "Unit Dose" Open System, No. 01-14398, Pfeiffer GmbH, Germany), (2) administered as nasal drops and (3) administered as a "splash" according to the invention by using the same nasal spray device as in (1), but having increased the viscosity of the aqueous solution with 1.0% (w/v) sodium carboxymethylcellulose (NaCMC).

Figure 4:
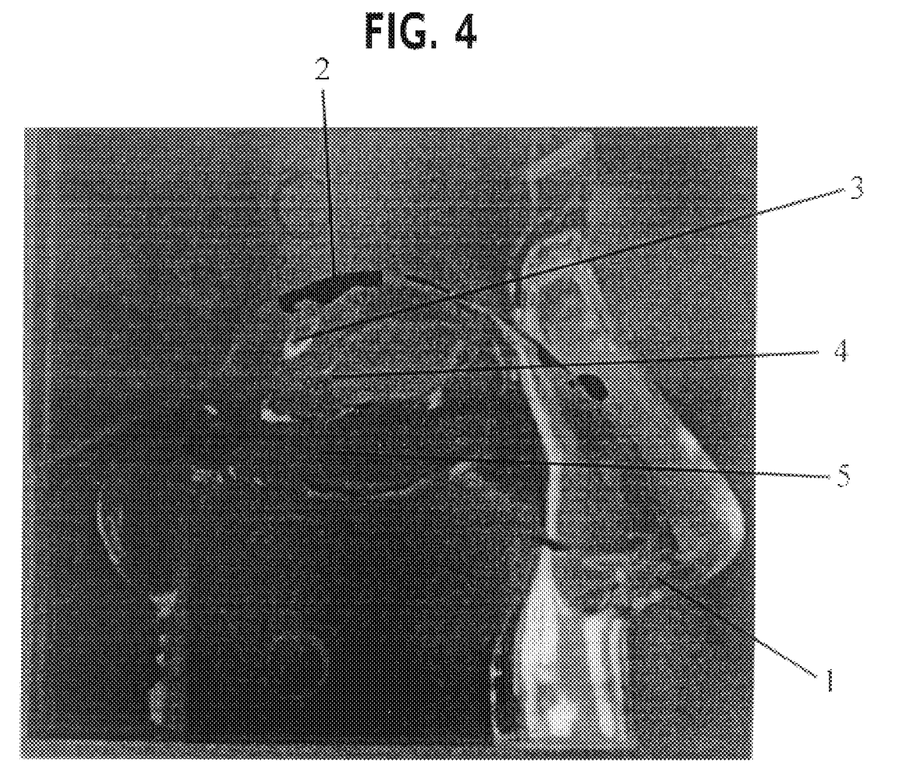
FIG. 4: Photograph showing the reconstructed human nose used in the experiments described herein.

The preparations were administered to the nasal cavity of a reconstructed human nasal cavity (made from silicone), wherein the olfactory region was covered with an absorbing paper (Watman 4 filter paper, Cat. No. 1004 090, Watman Int. Ltd., England). The human nasal model ("Koken nasal cavity model)" was obtained from Koken Co. Ltd. 3-14-3-Mejiro, Tokashima-ku, Tokyo 171, Japan, and the reconstructed human nose is depicted in FIG. 4, wherein 1 is the nostril and 2 is the olfactory region. The "bulges" 3, 4 and 5 are the superior, the middle and the inferior conchae, respectively. The "spot" located at the olfactory region 2 is caused by a dye which has been administered to the nasal cavity of the model as described in the succeeding Example 2.

After administration to the nasal cavity, the absorbing paper was removed, placed in a 10 ml tube, and the caffein was extracted with 2×9 ml water for 2 minutes after which the extract was diluted to 20 ml with water. The absorbance was measured at 273 nm and the amount of caffein was calculated from a standard curve. The deposited amount of caffein at the olfacory region was:

| Administration form | Recovered caffein[a] | Viscosity (cP) |
|---|---|---|
| Nasal spray: | 0.40% | 1 |
| Nose drops: | 0.00% | 1 |
| Nasal "splash" | ≧10% | 273 |

[a]The values indicate the amount of caffein deposited at the olfactory region in percent of the total amount administered.

The viscosity of the preparations were determined by means of a Brookfield Digital Viscometer, model DV-I+, version 2.0, at 25° after stabilisation for 30 min.

EXAMPLE 2

Accessibility to the Olfactory Region—the Influence of Viscosity

An aqueous solution containing 0.1% (w/v) brilliant blue dye (obtained from Delta Aromatic Egypt S.A.E, Giza, Egypt) was (1) administered using a conventional nasal spray device (Pfeiffer "Unit-Dose" Open System, No. 01-14398, Pfeiffer GmbH, Germany) and (2) administered as "splash" according to the invention by using the same nasal spray device as in (1), but having increased the viscosity of the aqueous solutions with various amounts of NaCMC.

The preparations were administered to the nasal cavity of a reconstructed human nasal cavity (made from silicone) as described in Example 1.

After administration to the nasal cavity, the absorbing paper was removed, placed in a 10 ml tube, and the dye was extracted with 2×4 ml water for 2 minutes after which the extract was diluted to 10 ml with water. The absorbance was measured at 630 nm and the amount of dye was calculated from a standard curve. The deposited amount of dye at the olfacory region was:

| NaCMC conc. (w/v) | Viscosity (cP) | Recovered dye[a] |
|---|---|---|
| 0 | 1 (water) | 0.40% |
| 0.2[b] | 22.0 | 22.2% ± 10.4 |
| 0.5[b] | 85.2 | 35.3% ± 14.1 |

[a]The values indicate the amount of dye deposited at the olfactory region in percent of the total amount administered.
[b]In addition to NaCMC these preparations also contained 1.0% (v/v) Tween 40 and 0.1% (v/v) diluendum methyl paraoxybenzoate.

The viscosity of the preparations were determined as described in Example 1.

EXAMPLE 3

The in Vitro Test—the Influence of Viscosity

Aqueous solutions without active substance but containing various amounts of NaCMC were subjected to the "In Vitro Delivery Test". The solutions were administered using a conventional nasal spray device (Pfeiffer "Unit-Dose" Open System, No. 01-14398, Pfeiffer GmbH, Germany). The results obtained were:

| NaCMC conc. (w/v) | Viscosity (cP) | Diameter[a] (cm) |
|---|---|---|
| 0 | 1 | 3.3 |
| 0.2 | 37.5 | 1.5 |
| 0.5 | 89.5 | 1.3 |
| 1.0 | 273 | 1.0 |

[a]The diameter indicates the diameter of a circle encompassing the area, wherein substantially the full amount of the ejected aqueous preparation was deposited.

The viscosity of the preparations were determined as described in Example 1.

EXAMPLE 4

The in Vitro Test—the Influence of Orifice Diameter of the Device

Water without active substance was subjected to the "In Vitro Delivery Test" and was administered using a conventional nasal spray device (Pfeiffer "Unit-Dose" Open System, No. 01-14398, Pfeiffer GmbH, Germany) having a nozzle diameter of 0.25 mm. In a second experiment the nozzle diameter of the device was adjusted to 0.70 mm by insertion of a needle (having an internal diameter of 0.70 mm) into the orifice of the device. The results obtained were:

| Viscosity (cP) | Diameter of nozzle orifice (mm) | Diameter[a] (cm) |
|---|---|---|
| 1 | 0.25 | 3.3 |
| 1 | 0.70 | 1.5 |

[a]The diameter indicates the diameter of a circle encompassing the area wherein substantially the full amount of the ejected aqueous preparation was deposited.

As it appears from the above examples it is not possible to get access to the olfactory region by using conventional devices comprising aqueous preparations of low viscosity. In order to be able to administer clinical relevant amounts of drugs to the olfactory region and, consequently, to the brain, it is necessary to adjust the device and/or the preparations in such a way that the spray angle (or the diameter referred to in the in vitro test) is reduced significantly compared to conventional nasal administration. Two "key" parameters have been identified, namely 1) the viscosity of the preparation to be administered and 2) the nozzle diameter of the device. The above examples clearly demonstrate that increasing the viscosity and/or the nozzle diameter leads to a significant reduced spray angle which is a prerequisite for successful nasal administration of drugs to the olfactory region.

What is claimed is:

1. A method for administering a pharmaceutical preparation comprising at least one active substance to the olfactory region of a human, the method comprising administering a unit dose of the pharmaceutical preparation by ejection from a nozzle of a spray device through a nostril of the human, the device being positioned so that a nozzle orifice of the nozzle is positioned approximately at the orifice of the nostril or in the *vestibulum nasi*, the device and the pharmaceutical preparation being adapted so that, when the nasal spray device comprising the pharmaceutical preparation is subjected to the test "In vitro Delivery Test" which comprises a) placing said spray device comprising said nozzle orifice and the pharmaceutical preparation to be delivered, so that said nozzle orifice of the device points straight up, b) placing a water absorbent surface which is adapted to receive and substantially immediately absorb a spray or droplets 3 cm above, and perpendicular to, said nozzle orifice of the device, and c) ejecting a unit dose of the pharmaceutical preparation from the device and thereby applying it to the water absorbent surface by normal actuation of the device, d) determining the diameter of a region within which substantially all of the unit dose is delivered by measuring the diameter of the smallest circle which encompasses the area of the water absorbent surface which has been wetted by the pharmaceutical preparation, and e) assessing the delivery of at least a particular percentage of the unit dose within a region of the deposited unit dose excising the circle from the surface, extracting the active substance from the excised area and measuring it quantitatively by spectrophotometry, the result of said test is utilized to deposit substantially the total amount of the unit dose in a region having a diameter of at most 2 cm.

2. The method a to claim 1, wherein the pharmaceutical preparation is in the form of a liquid.

3. The method according to claim 1, wherein the diameter of the nozzle orifice is in the range from 0.1 to 1.0 mm.

4. The method according to claim 3, wherein the diameter of the nozzle orifice is in the range from 0.2 to 0.8 mm.

5. The method according to claim 4, wherein the diameter of the nozzle orifice is in the range from 0.25 to 0.7 mm.

6. The method according to claim 1, wherein the pharmaceutical preparation contains a viscosity enhancing agent.

7. The method according to claim 6, wherein the viscosity enhancing agent is selected from the group consisting of polysaccharide and derivatives thereof, acrylic polymers, proteins, high average molecular weight polyhydroxy compounds, glycols and derivatives thereof.

8. The method according to claim 7, wherein the viscosity enhancing agent is selected from the group consisting of hydroxypropyl cellulose, hydroxypropyl methylcellulose, hydroxyethyl methylcellulose, carboxymethylcellulose and salts thereof, Carbopol, poly(hydroxyethyl methacrylate), poly(methoxyethyl methacrylate), poly(methoxyethoxyethyl methacrylate), gelatine, polyvinyl alcohol, propylene glycol, PEG 200, PEG 300, PEG 400, PEG 600, PEG 700, PEG 800, PEG 900, PEG 1000, PEG 1450, PEG 3350, PEG 4500, PEG 800 and derivatives thereof.

9. The method according to claim 8, wherein the viscosity enhancing agent is carboxymethylcellulose or sodium carboxymethylcellulose.

10. The method according to claim 6, wherein the viscosity enhancing agent is present in the pharmaceutical preparation in a concentration from about 0.01% (w/v) to about 10% (w/v).

11. The method according to claim 10, wherein the viscosity enhancing agent is present in the pharmaceutical preparation in a concentration from about 0.05% (w/v) to about 5% (w/v).

12. The method according to claim 6, wherein the dynamic viscosity of the pharmaceutical preparation is in the range of 5–300 cP at 25° C.

13. The method according to claim 12, wherein the dynamic viscosity of the pharmaceutical preparation is in the range of 5–100 cP.

14. The method according to claim 13, wherein the dynamic viscosity of the pharmaceutical preparation is in the range of 10–75 cP.

15. The method according to claim 14, wherein the dynamic viscosity of the pharmaceutical preparation is in the range of 10–50 cP.

16. The method according to claim 1, wherein the pharmaceutical preparation contains an odorant.

17. The method according to claim 16, wherein the odorant is present in the pharmaceutical preparation in a concentration of at the most 0.01% (w/w).

18. The method according to claim 1, wherein the pharmaceutical preparation further comprises at least one pharmaceutically acceptable excipient.

19. The method according to claim 1, wherein the device and the pharmaceutical preparation are adapted so that in said In vitro Delivery Test, substantially the full amount of the unit dose will be deposited in a region having a diameter of at the most 1.8 cm.

20. The method according to claim 19, wherein the device and the pharmaceutical preparation are adapted so that in said In vitro Delivery Test, substantially the full amount of the unit dose will be deposited in a region having a diameter of at the most 1.4 cm.

21. The method according to claim 20, wherein the device and the pharmaceutical preparation are adapted so that in said In vitro Delivery Test, substantially the full amount of the unit dose will be deposited in a region having a diameter of at the most 1.2 cm.

22. The method according to claim 21, wherein the device and the pharmaceutical preparation are adapted so that in said In vitro Delivery Test, substantially the full amount of the unit dose will be deposited in a region having a diameter of at the most 1.0 cm.

23. The method according to claim 1, wherein the device and the pharmaceutical preparation are adapted so that in said In vitro Delivery Test, at least 50% of the unit dose will be deposited in a region having a diameter of at the most 1.8 cm.

24. The method according to claim 23, wherein the device and the pharmaceutical preparation are adapted so that in said In vitro Delivery Test, at least 50% of the unit dose will be deposited in a region having a diameter of at the most 1.0 cm.

25. The method according to claim 1, wherein the pharmaceutical preparation is in the form of a powder having a mean particle size in the range from about 0.1 $\mu$m to about 100 $\mu$m.

26. The method according to claim 25, wherein the mean particle size is in the range from about 0.5 $\mu$m to about 25 $\mu$m.

27. A method for treatment or prophylaxis of conditions or disorders in the brain or in the central nervous system, the method comprising administering an effective amount of an active substance to the olfactory region of a human, in a pharmaceutical preparation comprising said substance, by ejection from a nozzle of a spray device through a nostril of the human, the device being positioned so that a nozzle orifice of the nozzle is positioned approximately at the orifice of the nostril or in the *vestibulum nasi*, the device and the pharmaceutical preparation being adapted so that when the nasal spray device comprising the pharmaceutical preparation is subjected to the test "In vitro Delivery Test" which comprises a) placing said spray device comprising said nozzle orifice and the pharmaceutical preparation to be delivered, so that said nozzle orifice of the device points straight up, b) placing a water absorbent surface which is adapted to receive and substantially immediately absorb a spray or droplets 3 cm above, and perpendicular to, said nozzle orifice of the device, and c) ejecting a unit dose of the pharmaceutical preparation from the device and thereby applying it to the water absorbent surface by normal actuation of the device, d) determining the diameter of a region within which substantially all of the unit dose is delivered by measuring the diameter of the smallest circle which encompasses the area of the water absorbent surface which has been wetted by the pharmaceutical preparation, and e) assessing the delivery of at least a particular percentage of the unit dose within a region of the deposited unit dose, excising the circle from the surface, extracting the active substance from the excised area and measuring it quantitatively by spectrophotometry, the result of said test is utilized to deposit, substantially the total amount of the unit dose in a region having a diameter of at most 2 cm.

28. The method according to claim 27, wherein the active substance is a substance capable of treating, detecting, or preventing brain diseases or disorders.

29. The method according to claim 28, wherein the active substance is a substance capable of treating brain cancers and/or brain tumors.

30. The method according to claim 27, wherein the active substance is selected from the group consisting of antiviral substances, antiprion substances, antibacterial substances, antineoplastic substances, antiparasitic substances, anti-inflammatory substances, antifungal substances, stimulating substances, sedative substances, hypnotic substances, analgesic substances, anticonvulsive substances, antiemetic substances, anxiolytic substances, antidepressive substances, tranquilizing substances, cognition enhancing substances, metabolic stimulating or inhibiting substances, appetite simulators or inhibitors, narcotic antagonists or agonists, nutrients, metabolic precursors for producing neurotransmitters, insulin and mixtures thereof.

31. The method according to claim 30, wherein the active substance is insulin.

32. The method according to claim 27, wherein the pharmaceutical preparation is in the form of a liquid.

33. The method according to claim 27, wherein the diameter of the nozzle orifice is in the range from 0.1 to 1.0 mm.

34. The method according to claim 33, wherein the diameter of the nozzle orifice is in the range from 0.2 to 0.8 mm.

35. The method according to claim 34, wherein the diameter of the nozzle orifice is in the range from 0.25 to 0.7 mm.

36. The method according to claim 27, wherein the pharmaceutical preparation contains a viscosity enhancing agent.

37. The method according to claim 36, wherein the viscosity enhancing agent is selected from the group consisting of polysaccharides and derivatives thereof, acrylic polymers, proteins, high average molecular weight polyhydroxy compounds, glycols and derivatives thereof.

38. The method according to claim 37, wherein the viscosity enhancing agent is selected from the group consisting of hydroxypropyl cellulose, hydroxypropyl methylcellulose, hydroxyethyl methylcellulose, carboxymethylcellulose and salts thereof, Carbopol, poly (hydroxyethyl methacrylate), poly(methoxyethyl methacrylate), poly(methoxyethoxyethyl methacrylate), gelatine, polyvinyl alcohol, propylene glycol, PEG 200; PEG 300, PEG 400, PEG 500, PEG 600, PEG 700, PEG 800, PEG 900, PEG 1000, PEG 1450, PEG 3350, PEG 4500, PEG 8000 and derivatives thereof.

39. The method according to claim 38, wherein the viscosity enhancing agent is carboxymethylcellulose or sodium carboxymethylcellulose.

40. The method according to claim 36, wherein the viscosity enhancing agent is present in the pharmaceutical preparation in a concentration from about 0.05% (w/v) to about 5% (w/v).

41. The method according to claim 36, wherein the dynamic viscosity of the pharmaceutical preparation is in the range of 5–100 cP.

42. The method according to claim 41, wherein the dynamic viscosity of the pharmaceutical preparation is in the range of 10–75 cP.

43. The method according to claim 42, wherein the dynamic viscosity of the pharmaceutical preparation is in the range of 10–50 cP.

44. The method according to claim 27, wherein the device and the pharmaceutical preparation are adapted so that in said In vitro Delivery Test, substantially the full amount of the unit dose will be deposited in a region having a diameter of at the most 1.8 cm.

45. The method according to claim 44, wherein the device and the pharmaceutical preparation are adapted so that in said In vitro Delivery Test, substantially the full amount of the unit dose will be deposited in a region having a diameter of at the most 1.4 cm.

46. The method according to claim 45, wherein the device and the pharmaceutical preparation are adapted so that in said In vitro Delivery Test, substantially the full amount of the unit dose will be deposited in a region having a diameter of at the most 1.0 cm.

47. The method according to claim 27, wherein the device and the pharmaceutical preparation are adapted so that in said In vitro Delivery Test, at least 50% of the unit dose will be deposited in a region having a diameter of at the most 1.8 cm.

48. The method according to claim wherein the device and the pharmaceutical preparation are adapted so that in said In vitro Delivery Test, at least 50% of the unit dose will be deposited in a region having a diameter of at the most 1.0 cm.

49. A nasal spray device containing an amount of a pharmaceutical preparation which contains an odorant and being adapted for ejecting a unit dose of the pharmaceutical preparation from a nozzle of the spray device through a nostril of a human on actuation of the device, the device having audiameter of a nozzle orifice of the nozzle in the range of 0.1–1.0 mm and the pharmaceutical preparation comprising a viscosity enhancing agent and having a dynamic viscosity in the range of 5–300 cP at 25° C., the device and the pharmaceutical preparation being adapted so that, when the nasal spray device comprising the pharmaceutical preparation is subjected to an In vitro Delivery Test which comprises:

a) placing said spray device comprising said nozzle orifice and the pharmaceutical preparation to be delivered, so that said nozzle orifice of the device points straight up, b) placing a water absorbent surface which is adapted to receive and substantially immediately absorb a spray or droplets 3 cm above, and perpendicular to, said nozzle orifice of the device, and c) ejecting a unit dose of the pharmaceutical preparation from the device and thereby applying it to the water absorbent surface by normal actuation of the device, d) determining the diameter of a region within which substantially all of the unit dose is delivered by measuring the diameter of the smallest circle which encompasses the area of the water absorbent surface which has been wetted by the pharmaceutical preparation, and e) assessing the delivery of at least a particular percentage of the unit dose within a region of the deposited unit dose, excising the circle from the surface, extracting the active substance from the excised area and measuring it quantitatively by spectrophotometry, substantially the total amount of the unit dose is deposited in a region having a diameter of at the most 2 cm.

50. The nozzle spray according to claim 49, wherein the odorant is present in the pharmaceutical preparation in a concentration of at the most 0.01% (w/w).

* * * * *